US012673160B2

(12) United States Patent
Nazzaro

(10) Patent No.: US 12,673,160 B2
(45) Date of Patent: *Jul. 7, 2026

(54) SECURE WIRELESS COMMUNICATIONS BETWEEN A GLUCOSE MONITOR AND OTHER DEVICES

(71) Applicant: INSULET CORPORATION, Acton, MA (US)

(72) Inventor: David Nazzaro, Groveland, MA (US)

(73) Assignee: INSULET CORPORATION, Acton, MA (US)

( * ) Notice: Subject to any disclaimer, the term of this patent is extended or adjusted under 35 U.S.C. 154(b) by 110 days.

This patent is subject to a terminal disclaimer.

(21) Appl. No.: 18/892,775

(22) Filed: Sep. 23, 2024

(65) Prior Publication Data

US 2025/0082850 A1     Mar. 13, 2025

Related U.S. Application Data

(63) Continuation of application No. 17/490,372, filed on Sep. 30, 2021, now Pat. No. 12,115,351.

(60) Provisional application No. 63/085,822, filed on Sep. 30, 2020.

(51) Int. Cl.

| | |
|---|---|
| *G06F 21/62* | (2013.01) |
| *A61M 5/142* | (2006.01) |
| *A61M 5/172* | (2006.01) |
| *H04W 12/03* | (2021.01) |
| *H04W 12/06* | (2021.01) |

(52) U.S. Cl.
CPC ...... *A61M 5/1723* (2013.01); *A61M 5/14244* (2013.01); *G06F 21/6245* (2013.01); *H04W 12/03* (2021.01); *H04W 12/06* (2013.01); *A61M 2205/3553* (2013.01)

(58) Field of Classification Search
CPC .. A61M 5/1723; H04W 12/03; G06F 21/6245
See application file for complete search history.

(56) References Cited

U.S. PATENT DOCUMENTS

| | | | | |
|---|---|---|---|---|
| 9,358,334 | B2 * | 6/2016 | Arefieg ................. | G16H 40/67 |
| 12,226,612 | B2 * | 2/2025 | Zheng .................... | G06F 17/17 |
| 2018/0182491 | A1 * | 6/2018 | Belliveau ........... | A61B 5/14503 |
| 2022/0096748 | A1 * | 3/2022 | El-Khatib ......... | A61M 5/14248 |
| 2025/0082850 | A1 * | 3/2025 | Nazzaro ............. | G06F 21/6245 |

* cited by examiner

*Primary Examiner* — Simon P Kanaan
(74) *Attorney, Agent, or Firm* — Goodwin Procter LLP

(57) ABSTRACT

The exemplary embodiments may provide a secure framework for devices in a drug delivery system to wirelessly communicate. The secure framework may use encrypted keys to carry credentials and to specify the rights of the devices presenting the credentials. The devices in the drug delivery system present the keys at the time that they wish to wirelessly communicate with other devices in the drug delivery system. The devices receiving such keys, decrypt the keys and verify if the credentials are valid. If the credentials are valid, a wireless communication session between devices may be established.

20 Claims, 12 Drawing Sheets

SECURE WIRELESS COMMUNICATIONS BETWEEN A GLUCOSE MONITOR AND OTHER DEVICES

CROSS-REFERENCE TO RELATED APPLICATIONS

This application is a continuation of U.S. patent application Ser. No. 17/490,372, filed Sep. 30, 2021, which claims the benefit to U.S. Provisional Application No. 63/085,822, filed Sep. 30, 2020, the entire contents of which are incorporated herein by reference in their entirety.

BACKGROUND

A typical conventional on-body insulin delivery system may include an insulin pump and a continuous glucose monitor (CGM). The insulin pump may contain insulin for delivery to a user under the control of a control algorithm. The insulin pump may be positioned on the body of the user. The CGM monitors blood glucose levels of the user on an on-going basis. The CGM, like the insulin pump, may be positioned on the body of the user. The insulin drug delivery system may also include a management device, like a dedicated handheld device or a smartphone, that runs a management application.

There may be certain communication limitations with such a conventional on-body insulin delivery system. For example, the CGM may require a Near Field Communication (NFC) capability to initialize the CGM and begin communications with the management device. For the case where the management device is a smartphone of a user that is not NFC capable, the phone is not able to initialize the CGM. In addition, such a conventional insulin delivery system may require that the management device act as an intermediary for communications between the insulin pump and the CGM. For instance, if the insulin pump wishes to read blood glucose level values stored in the CGM, the insulin pump may need to ask the management device to get the blood glucose level values from the CGM and return the retrieved blood glucose level values to the insulin pump. Due to security concerns, additional devices are not permitted to wirelessly communicate with the insulin pump or CGM.

SUMMARY

In accordance with an inventive aspect, a medicament delivery device includes a medicament supply and a pump for pumping the medicament from the medicament supply to a user. The device also includes a wireless transceiver for transmitting and receiving wireless communications. The device further includes a processor configured to receive a secure package from a requesting device via a wireless connection and extract contents of the secure package, including a key. The processor is further configured to validate the key as valid or not. Where the key is valid, wireless communications with the requesting device are permitted, and where the key is not valid, wireless communications with the requesting device are not permitted.

The processor may be further configured to generate an additional key for the medicament delivery device to wirelessly communicate with an additional device. The processor may be configured to generate a secure package containing the key and to send the secure package wirelessly to the additional device to request wireless communications with the additional device. The extracting of the contents of the secure package may involve at least one of decrypting the secure package, applying an inverse hash function to the secure package or reversing an obfuscation of the secure package. The extracting of the contents of the secure package may extract the key from the secure package and/or a timestamp. The validating the key may entail using the timestamp to determine whether the key has expired. The extracting of the contents of the secure package may involve extracting information regarding rights to be granted to the requesting device as to wireless communications. The requesting device may be one of a glucose monitor, a wearable device or a mobile computing device.

In accordance with an inventive aspect, an on-body medical device includes a wireless transceiver for transmitting and receiving wireless communications. The device also includes a processor configured to receive a secure package from a requesting device via a wireless connection and extract contents of the secure package, including a key. The processor is further configured to validate the key as valid or not. Where the key is valid, the processor permits wireless communications with the requesting device. Where the key is not valid, the processor does not permit wireless communications with the requesting device.

The extracting of the contents of the secure package may include at least one of decrypting the secure package, applying an inverse hash function to the secure package or reversing an obfuscation of the secure package. The extracting of the contents of the secure package may include extracting the key from the secure package and/or extracting a timestamp. The validating of the key may entail using the timestamp to determine whether the key has expired. The extracting of the contents of the secure package may include extracting information regarding rights to be granted to the requesting device as to wireless communications. The on-body medical device may be a glucose monitor or a drug delivery device In accordance with an inventive aspect, a device includes a wireless transceiver for transmitting and receiving wireless communications and a processor. The processor is configured to generate a secure package that is encrypted, hashed and/or obfuscated. The secure package contains a key for wireless communications. The processor also is configured to send the secure package wirelessly to request wireless communication to a target device. The target device is one of a drug delivery device, a biometric sensor, or a manager of a drug delivery device.

The secure package may contain a timestamp for the key. The secure package may contain identity information for the device. The secure package may contain information regarding the rights to be granted to the device regarding wireless communications.

BRIEF DESCRIPTION OF THE DRAWINGS

FIG. 1B depicts a block diagram illustrating communication links for devices in a drug delivery system of an exemplary embodiments

DETAILED DESCRIPTION

Figure 1A:
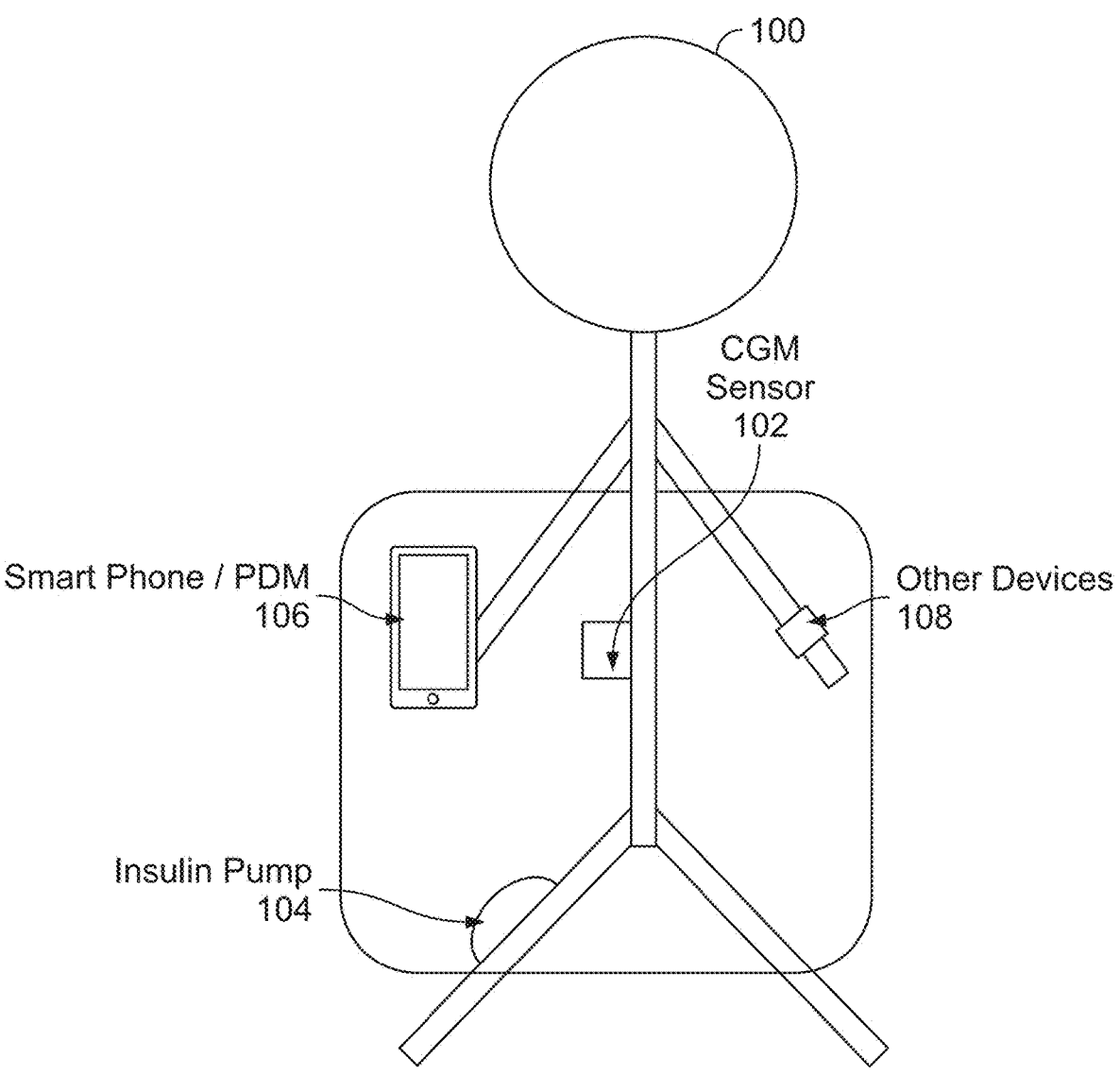
FIG. 1A depicts a diagram of a user with multiple illustrative devices for use in an exemplary embodiment.

The exemplary embodiments may provide a secure framework for devices in a drug delivery system to wirelessly communicate. The secure framework may use secure keys to carry credentials and to specify the rights of the devices presenting the credentials. The devices in the drug delivery system present the secure keys at the time that they wish to wirelessly communicate with other devices in the drug delivery system. The devices receiving such secure keys, process the keys and verify if the credentials are valid. If the credentials are valid, a wireless communication session between devices may be established. If not, a wireless communication session is not permitted.

The exemplary embodiments may eliminate the need for the management device of a drug delivery system to act as an intermediary for wireless communications among devices in the drug delivery system. Thus, an medicament pump may wirelessly communicate directly with the CGM. This may be helpful in creating a closed loop control system where the medicament pump receives blood glucose level readings directly from the CGM via wireless communications and feeds the received blood glucose level readings into the control algorithm of the medicament pump. In such circumstances, additional devices are unnecessary when the medicament pump and CGM are operating in a closed loop. After the medicament pump is activated the medicament pump and the CGM may operate in a closed loop fashion without other devices.

An additional benefit of use of the secure framework is that it allows additional devices to communicate with the CGM and medicament pump. For example, a wearable device, such as a smart watch, smart ring or smart bracelet, may communicate with the CGM or medicament pump if the wearable device contains the proper credentials. The wearables may provide some of the functionality that is otherwise provided exclusively by the management device. This may be easier from some users as opposed to needing to carry the management device as the users move about. Moreover, the form factors of the wearable devices may make them more convenient than the management device when performing activities such as exercising. Still further, the wearable device may be more discrete than the management device. A user can look at a wearable for a current blood glucose reading more discretely than a larger management device that is handheld. Also, since the wearable is worn on-body, the user does not have to be concerned with leaving the wearable behind once the wearable is secured to the user.

The ability of additional devices to be validated and communicate with the medicament pump or CGM also expands the possible configurations of the drug delivery system. For example, biometric sensors, like blood pressure sensors, heart rate sensors, galvanic sensors and accelerometers, if not already built into the medicament pump or CGM, may be set up to wirelessly communicate with the medicament pump and provide useful inputs to the control algorithm for the medicament pump. Also, the CGM may output blood glucose level readings to smart watches, tablet computers and other devices for display and analysis.

The exemplary embodiments are described below relative to a drug delivery system that delivers a medicament, such as insulin, a GLP-1 agonist or pramlintide. As a result, in the discussion below the drug delivery device is an insulin pump, and the sensor is a CGM. Nevertheless, it should be appreciated that the secure framework may also be used with other types of drug delivery systems that deliver agents such as pain management agents, chemotherapy agents, antibiotics, therapeutic agents, etc., and that deploy different biometric sensors as part of a continuous biometric meter or CBM.

FIG. 1A depicts an illustrative user 100 of a glucose monitor 102 with a number of devices that are being either carried by the user 100 or are attached to the user 100. The devices 102, 104, 106 and 108 may all be part of a medicament delivery system. The depiction is intended to be merely illustrative and not limiting. The glucose monitor 102 is a sensor that is an on body device that is affixed to the user 100. The glucose monitor 102 provides regular blood glucose level readings via a sensor placed under the skin of the user 100. The glucose monitor 102 may be a CGM. The user 100 has a management device realized as a smartphone or a personal diabetes monitor (PDM) 106. The PDM 106 is a handheld device that is dedicated for use with an insulin pump 104. An example of the insulin pump 104 is the Omnipod from Insulet Corporation. The smartphone/PDM 106 may be held by the user 100 or be in the possession of the user, such as on the user's belt or in the user's pocket. The insulin pump 104 may be secured to the user, such as on a user's abdomen or on the user's leg, as shown in FIG. 1A. The insulin pump 104 is a medicament delivery device that delivers insulin to the user. The insulin pump 104 may include a needle, a cannula and tubing or the like for providing a pathway for delivering the drug (e.g., insulin) to the user 100. In this example, an example of one of the other devices 108 is shown being worn on the wrist of the user 100. The other devices 108 may include a wearable device, such as a smart watch, a smart bracelet or a smart ring. That said, the other devices 108 need not include a wearable device but more generally may include a device that is capable of wireless communication and is able to participate in the secure framework for wireless communication as will be described in more detail below. The other devices 108 may include an NFC-enabled and/or BLE-enabled device.

Figure 1B:
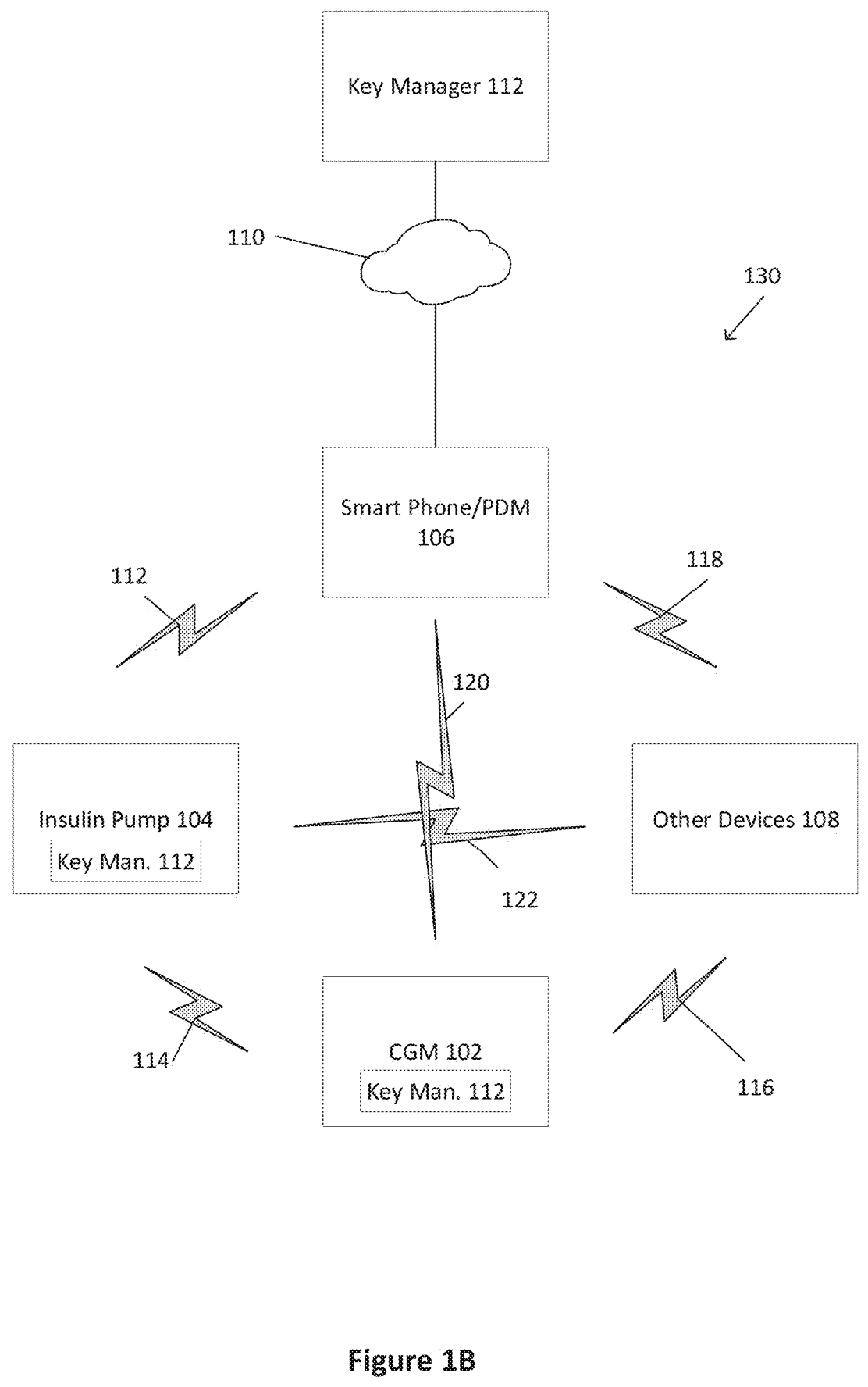

FIG. 1B depicts a block diagram of the medicament delivery system 130 for the components 102, 104, 106 and 108 shown in FIG. 1A. The other devices 108 are intended to represent any device that is capable of wirelessly communicating with the other components in the drug delivery system. The other devices 108 may be a wearable device, a sensor, a fob, a tablet computer, a mobile computing device, a desktop computing device, an instrument with wireless capability or the like. In exemplary embodiments, wireless connections 112, 114, 116, 118, 120 and 124 may be established between pairs of these components in accordance with the secure framework. This enables each of the components 102, 104, 106 and 108 to wirelessly communicate with the other components. The depiction in FIG. 1B depicts total wireless connectivity between each pair of the components 102, 104, 106 and 108. In some exemplary embodiments, only a subset of the wireless connections 112, 114, 116, 118, 120 and 122 need to be established.

As can be seen in FIG. 1B, there is no longer the need for the smart phone/PDM 106 to act as an intermediary for wireless communications. Thus, for example, the insulin pump 104 may directly communicate with the CGM 102 via a wireless connection 114. As was mentioned above, the direct wireless connection 114 between the CGM and the insulin pump 104 may facilitate a control loop where blood glucose level readings from the CGM 102 are fed to the insulin pump 104 and serve as input to a control algorithm of the insulin pump 104 that adjusts insulin delivery amounts and/or timing based on the blood glucose level readings. In addition, additional devices, like other devices 108, may communicate with the devices 102, 104 and 106 in the medicament delivery system 130. As a result, the other devices 108 may, for example, display blood glucose level readings or insulin deliver history information or issue commands to the insulin pump 104 in some exemplary embodiments, such as when operating in an open-loop control fashion.

The smart phone/PDM 106 may have a connection to a network 110, such as an Internet connection, a virtual private network (VPN), a Local Area Network (LAN), a cellular phone network or a combination thereof. The connection to the network 110 provides access to a key manager 112. The key manger 112 may be resident on a server and may be provided as a cloud service in some exemplary embodiments. The key manager 112 alternatively may be resident locally, such as on the insulin pump 104 or on the CGM 112 as shown in. The key manager 112 is responsible for generating keys that are for use in the secure framework. As will be described in more detail below, the key manager 112 is responsible for generating keys that are used to establish wireless connections, like wireless connections 112, 114, 116, 118, 120 and 122, in the medicament delivery system 130. The keys may be provided upon request of the smart phone/PDM 106, insulin pump 104, CGM 102, or other devices 108.

As was discussed above, the exemplary embodiments may use devices other than a smartphone/PDM 106 to initialize an uninitialized glucose monitor 106 or to awaken a sleeping glucose monitor 106. The other devices 108 may include, for example, wearables like a smartwatch or ring, a tablet, a fob, a smart pager, a notebook computer, a badge or a tag. The other devices 108 may be able to communicate using the desired wireless protocol (e.g., NFC) such that it can perform the functionality described above. The secondary or other device 108 may have a form factor (e.g. size, weight, etc.) that lends itself to convenient use in interacting with the glucose monitor 106, or insulin pump 104, or CGM 102.

Figure 2A:
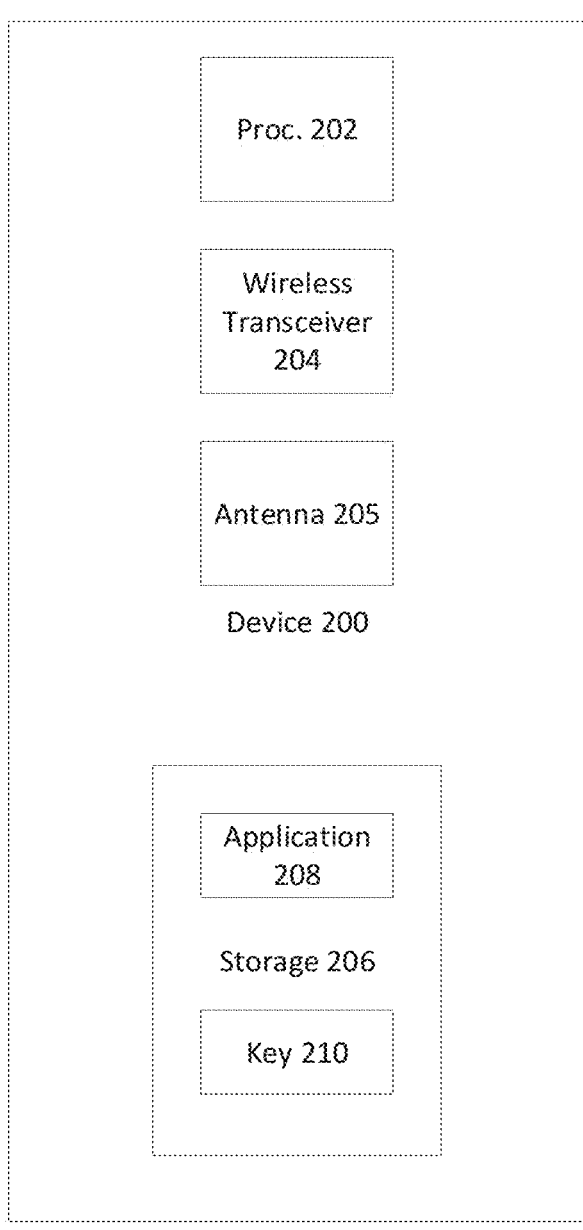
FIG. 2A depicts a block diagram of an illustrative device in the drug delivery system of an exemplary embodiment.

FIG. 2A shows a generalized block diagram of components of a device 200 that participates in wireless communication with at least one component in a drug delivery system like medicament delivery system 130 depicted in FIG. 1B. CGM 102, insulin pump 104, smartphone/PDM 106 and other devices 108 are examples of such a device 200. The device 200 includes a processor 202 like a Central Processing Unit (CPU), a Graphics Processing Unit (GPU), an Application Specific Integrated Circuit, a Field Programmable Gate Array (FPGA), a System on a Chip (SoC), or other processing component. The processor 202 may execute computer programming instructions, like application 208. The application 208 may contain instructions for performing the functionality described herein relating to establishing wireless connections, generating secure packages with keys and validating keys. Each device that wishes to participate in a secure framework must run the application 208 or have equivalent functionality performed by another program, applet, module, library, routine, object, method function or the like. Wireless transceiver 204 facilitates wireless communications by transmitting and receiving communications via an antenna 205. The wireless transceiver may communicate using one or more wireless protocols, such as the Bluetooth wireless protocol, the Bluetooth Low Energy (BLE) protocol, the WiFi (IEEE 802.11) wireless protocol, the Near Field Communication (NFC) wireless protocol, the Wireless Body Area Network (WBAN) wireless protocol (IEEE 802.15.6) or other wireless protocol. Multiple wireless transceivers for different protocols may be provided in some embodiments.

A storage 206 may be provided for storing computer programs, computer program instructions and/or data. The storage may store the application 208 and a secure key 210 that is used in the secure framework described herein. The storage may include Random Access Memory (RAM), Read Only Memory (ROM), flash memory, magnetic disk storage, optical disk storage, solid state storage, computer-readable storage media, registers or the like.

Figure 2B:
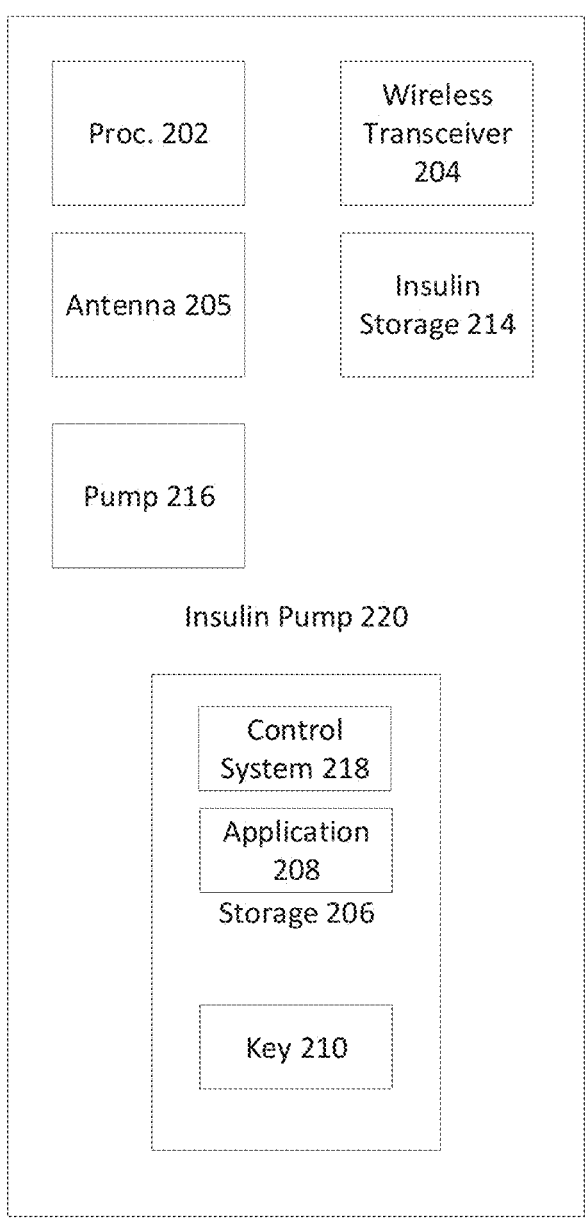
FIG. 2B depicts a block diagram of a medicament pump of an exemplary embodiment.

FIG. 2B depicts a more detailed block diagram of an insulin pump 220 of an exemplary embodiment. Like the device 200 (which, again, may represent an insulin pump), the insulin pump 220 contains a processor 202, a wireless transceiver 204, an antenna 205, a storage 206, application 208, a secure key 210 as described above relative to FIG. 2A. The insulin pump 220 also contains an insulin storage 214 for storing the insulin to be delivered to the user and a pump 216 for pumping the insulin out of the insulin storage 214 to the user. In addition, the storage 206 stores computer programming instructions for implementing the control system functionality 218. These instructions 218 implement the control algorithm that controls delivery of insulin to the user.

Figure 3:
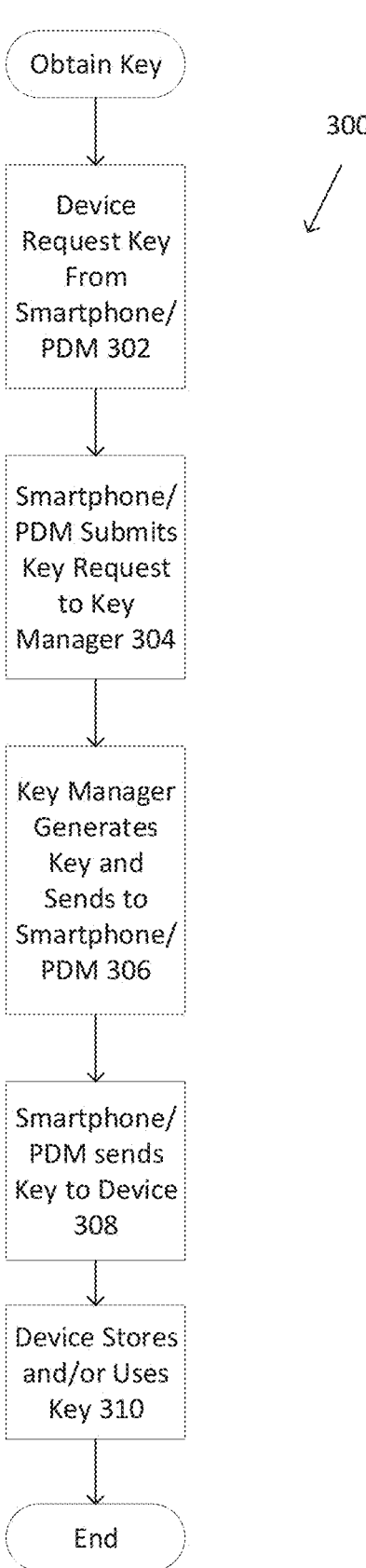
FIG. 3 depicts a flowchart of steps that may be performed in an exemplary embodiment to obtain a secure key for wireless communication.

FIG. 3 depicts a flowchart of steps that may be performed in an exemplary embodiment to obtain a secure key for wireless communication. The process may begin with a request from a device for a secure key that is sent to the smartphone/PDM 106 (302). Alternatively, no request may be required, or all devices may be provided secure keys at boot time in alternative embodiments. The smartphone/PDM 106 is responsible for getting such secure keys and distributing the secure keys to the devices 102, 104, 106 and 108. The smartphone/PDM submits the request to the key manager 112 (304). The key manager 112 generates the secure key and sends the secure key to the smartphone/PDM 106 (306). The generation may entail retrieving the secure key from secure storage or generating the secure key on demand. The smartphone/PDM 106 sends the secure key to the requesting device (308). The requesting device may store the secure key and/or use the secure key once received to establish wireless communication with one of the devices 102, 104, 106 or 108 (310).

Figure 4A:
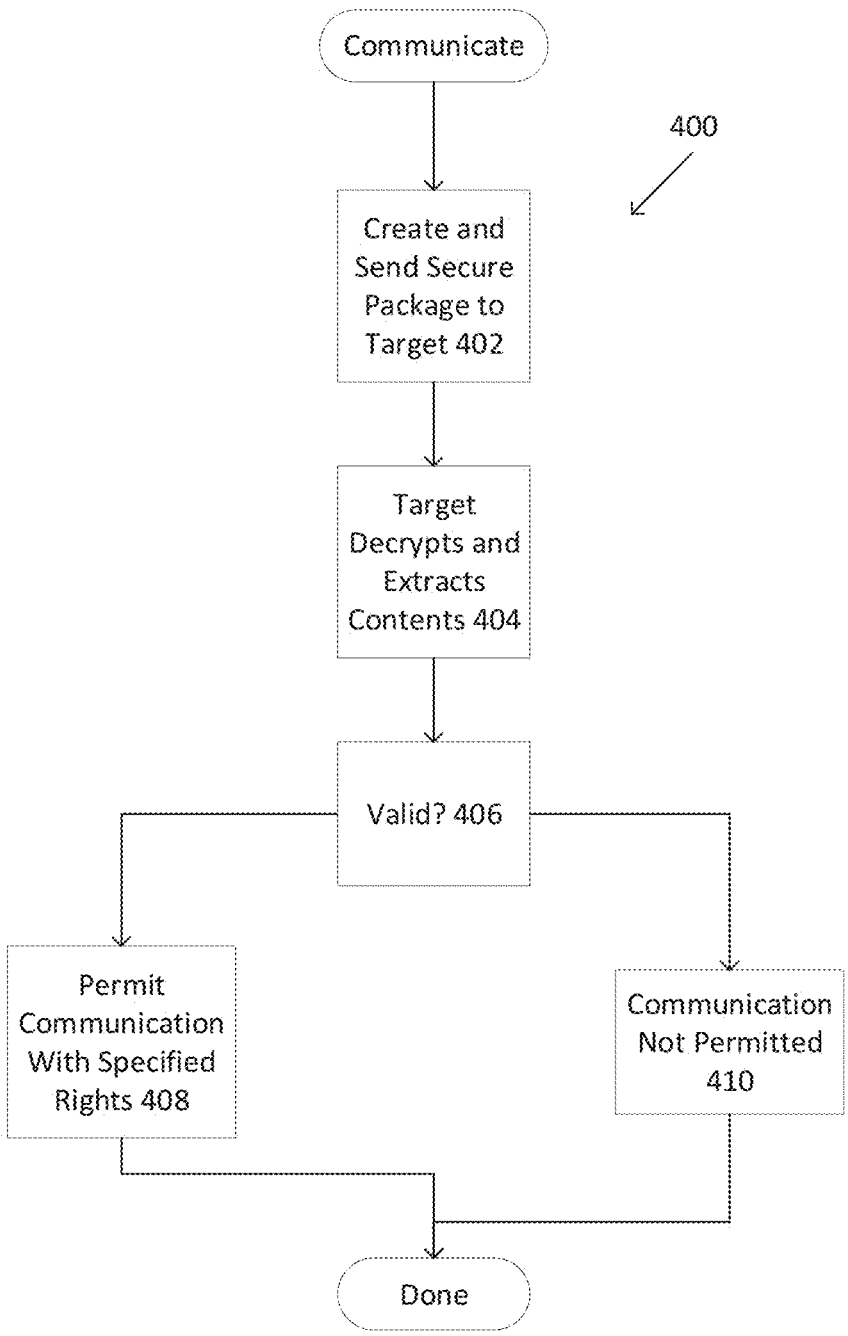
FIG. 4A depicts a flowchart of illustrative steps that may be performed to get permission to wirelessly communicate in an exemplary embodiment.
Figure 4B:
FIG. 4B depicts a diagram of elements of a secure package in an exemplary embodiment.

FIG. 4A depicts a flowchart 400 of illustrative steps that may be performed to establish a wireless communication connection using a secure key. The requesting device that wishes to communicate creates and sends a secure package to the target device (402). FIG. 4B shows an example of illustrative contents for the secure package 420. The package may be secure in that it may be hashed, encrypted and/or otherwise obfuscated to ensure that an unauthorized listener cannot determine the contents of secure package 420. The secure package may contain identification information 422 for the requesting device. The secure package 420 may contain a secure key 424. The secure key 424 may be an encrypted value that serves as a credential. The secure package 420 may also contain information regarding the privileges of the requesting device 426. These privileges might be, for example, a read privilege where the requesting device may read information from the target device but not modify any information. The rights 426 may specify a write privilege, which enables the requesting device to write information in the storage of the target device. The rights 426, in some instances, may specify both read and write privileges for a requesting device. It should be appreciated that the rights may specify other parameters, such as what information types or particular data may be viewed or modified. The rights 426 may specify whether the requesting device is able to send commands to the target device. A payload 428 may be provided as part of the secure package 420. The payload 428 may contain messages, data, commands or other information that is to be sent to the target device. The secure package 420 may also include a timestamp 430. The timestamp 430 may specify how long the secure key 424 is good for or when the key 424 was created. After expiration of a designated time period, the secure key 424 may no longer be valid for use.

After the secure package 420 is sent from the requesting device to the target device (402), the target device decrypts and otherwise reverses the obfuscation of the secure package 420. The target device may have a suitable decryption key, reverse hash function or the like to perform the decryption and/or obfuscation. The target device extracts the contents of the secure package (404). The extraction may include decrypting the secure key 424. The target device may check whether the key 424 is valid (406). The target device possesses knowledge of what a decrypted key value should be and can check whether the decrypted value is correct and valid. Moreover, the target device may use the timestamp 430 to check whether the key 424 has expired as part of checking the validity of the key 424. If the key is determined to be valid, a connection with the requesting device is permitted (408). The requesting device may have the privileges specified by the rights 426. If the key is determined to be invalid, the request to establish a connection is denied by the target device so that wireless communication is not permitted (410). The functionality specified in the flowchart 400 may be realized as part of the application 208.

This ability provided by the secure framework for additional devices to wirelessly communicate with other components in the drug delivery system may help address the problem where a smartphone cannot initialize a CGM because the smartphone lacks NFC capability. With the secure framework another device that has NFC capability may be used to initialize or activate the CGM, or in some cases, the insulin pump.

Figure 5A:
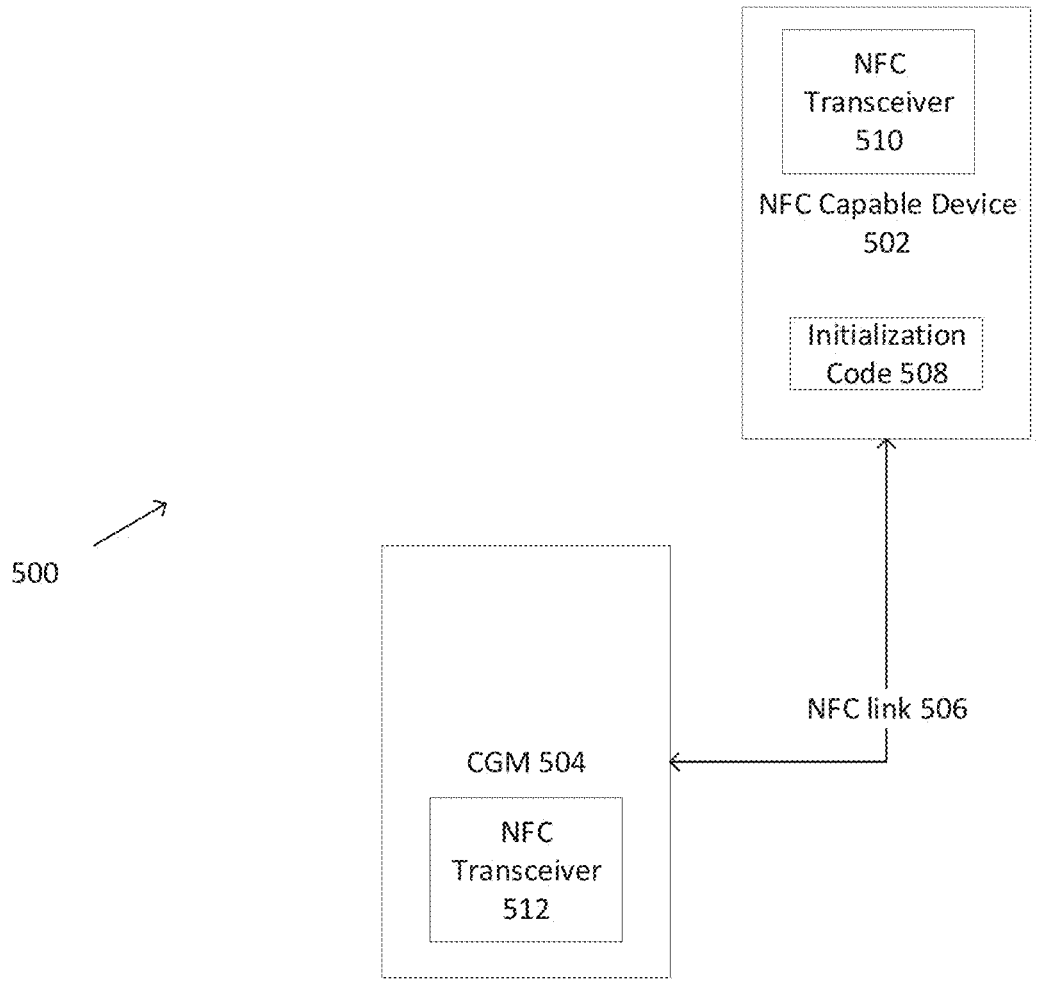
FIG. 5A depicts a block diagram showing how an NFC capable device may initialize a CGM in an exemplary embodiment.
Figure 5B:
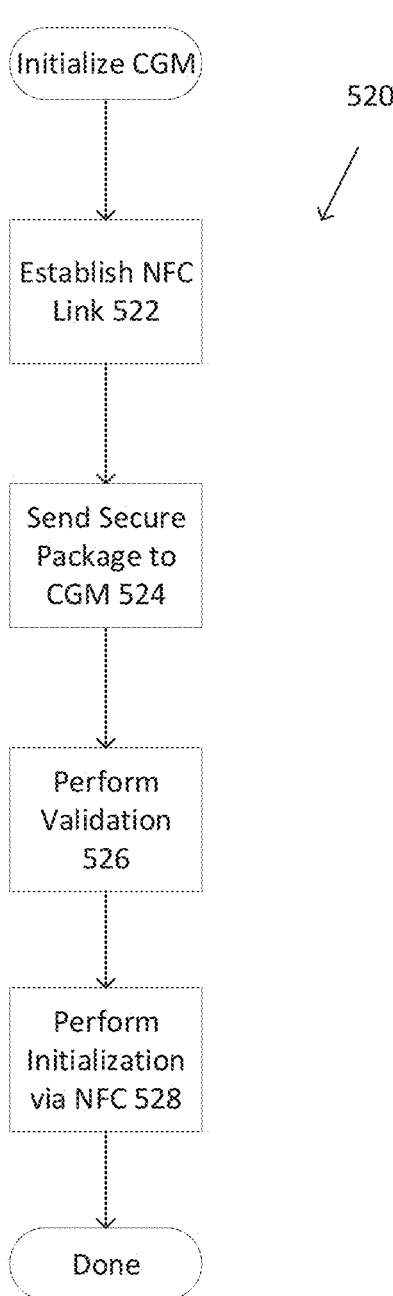
FIG. 5B depicts a flowchart of illustrative steps that may be performed to initialize a CGM with an NFC capable device in an exemplary embodiment.

FIG. 5A depicts a diagram 500 showing an instance in an exemplary embodiment wherein an NFC-capable device 502, e.g., a smartwatch, is used in initializing and awakening (or activating) the CGM 504. The process begins as shown in the flowchart 520 of FIG. 5B. Initially, an NFC link 506 is established between the NFC-capable device 502 and the CGM 504 by placing the NFC-capable device 502 in close proximity with the CGM 504 (522). The NFC transceivers 510 and 512 in the NFC-capable device 502 and the CGM

504 automatically establish the NFC link 506 when placed in proximity with each other. The NFC-capable device 502 then sends a secure package like the secure package 420 that was described with reference to FIG. 4B to the CGM 504 (524). The CGM 504 performs validation of the key as described above relative to FIG. 4A (526). Since the NFC-capable device 502 has a valid key, the communication session is allowed. The NFC-capable device 502 has initialization code 508 that permits it to take the necessary steps via the NFC link 506 to initialize the CGM 504 (528). This initialization code 508 may be like that found on a conventional NFC capable smartphone which is configured to enable initialization or activation of the CGM 504. Once initialized, the CGM 504 is free to communicate with other devices. An identical operation may be performed with an insulin pump having an NFC transceiver.

Figure 6:
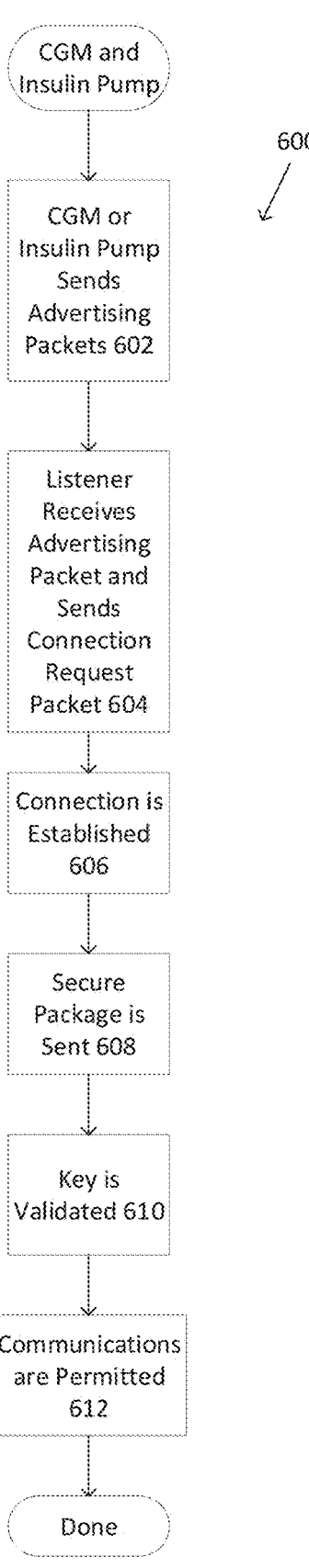
FIG. 6 depicts a flowchart of illustrative steps that may be performed to create a wireless connection between a medicament pump and a CGM in an exemplary embodiment.

As was mentioned above, one advantage provided by the secure framework is that the CGM 102 is able to wirelessly communicate with the insulin pump 104. FIG. 6 provides a flowchart 600 of illustrative steps that may be performed for the CGM 102 and the insulin pump 104 to communicate via BLE. With BLE, the pairing process begins with a device sending out advertising packets on advertising channels. BLE uses 40 channels that are separated in the frequency domain. Three of these channels are designated for advertising. In this example, either the CGM 102 or the insulin pump 104 sends out advertising packets (602). This device is known as the peripheral device or the "peripheral." The other device 102 or 104 listens and receives the advertising packets. The listening device is known as the central device or the "central." The central sends out a connection request packet (604) to the peripheral. A connection is then established (606). However, in the secure framework, the peripheral must present a valid key to continue to wirelessly communicate. To that end, a secure package is sent from the peripheral to the central (608). The key is extracted and validated (610) as has been described above. Wireless communications via BLE between the CGM 102 and the insulin pump are then permitted (612).

Figure 7:
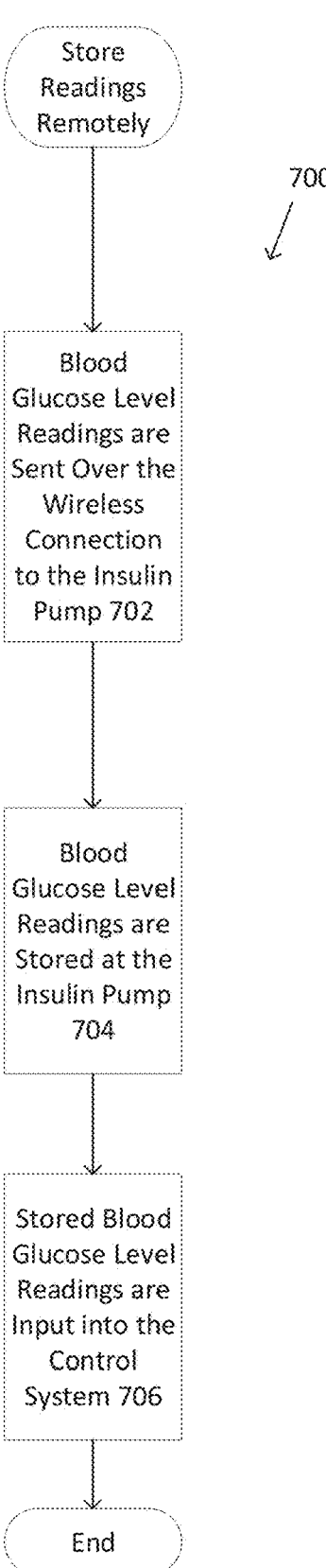
FIG. 7 depicts a flowchart showing illustrative steps that may be performed to store blood glucose level readings at a medicament pump in an exemplary embodiment.

As was mentioned above, the wireless connection between the CGM 102 and insulin pump 104 may be used to realize closed loop control of insulin delivery to the user 100 without involvement of other devices. FIG. 7 provides a flowchart 700 of how the wireless connection for realizing such closed loop control is used. The CGM 102 generates blood glucose level readings. These readings are sent over the wireless connection from the CGM 102 to the insulin pump 104 (702). The blood glucose level readings may be stored at the insulin pump 104 in storage (704). The stored blood glucose level readings may then be used as input into the control system (706). CGM 102 or insulin pump 104 may optionally transmit the blood glucose level readings to other devices for display or tracking purposes. Additionally, the insulin pump 104 may similarly transmit data around insulin delivery (e.g., amount and/or timing of insulin delivered, as basal or bolus amounts, amount of "insulin on board," amount of insulin remaining in reservoir, amount of insulin used, amount of battery charge remaining, estimated expiration of insulin pump 104 based on factors such as amount of insulin remaining in reservoir and/or amount of energy remaining in batteries on insulin pump).

Another benefit of the secure framework is that it allows different devices to have different rights. It may be desirable for security purposes to limit the rights of some devices. One example of this is that a device may only have read rights (viewing rights). For instance, a requester may be granted viewing rights from a target but not write privileges. Hence, the requester can only view information from the target but cannot change values stored on the target or issue commands to the target. Thus, for example, a device may request viewing privileges to receive blood glucose level readings from the CGM 102. Similarly, a device may be granted viewing rights from the insulin pump 104, but not write (or command) privileges. Hence, the requester can only view certain data (such as that identified in the preceding paragraph), but cannot change values stored on the insulin pump 104 or issue commands to the insulin pump 104.

Figure 8:
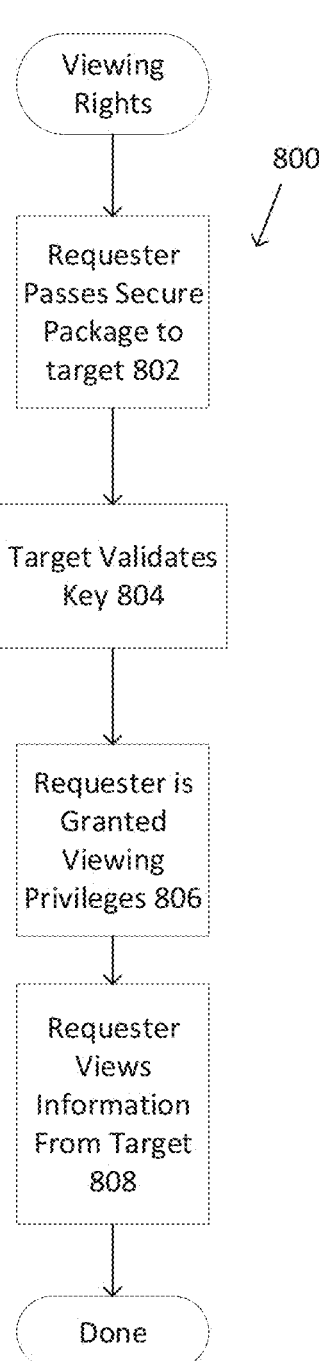
FIG. 8 depicts a flowchart showing illustrative steps that may be performed to obtain viewing rights from a CGM in an exemplary embodiment.

FIGS. 8 show a flowchart 800 of illustrative steps that may be performed in such an instance. Initially, the device that is the requester passes a secure package to the device that is the target (802). The secure package contains a valid key that has not expired and specifies the rights as read privileges ("viewing privileges"). The target validates the key as discussed above (804). The requester is granted viewing privileges (806). The requester may then view information from the target (808).

While the present invention has been described with reference to exemplary embodiments herein, those skilled in the art will appreciate that various changes in form and detail may be made without departing from the intended scope as defined in the appended claims.

The invention claimed is:

1. A glucose monitor, comprising:
a wireless transceiver for transmitting and receiving wireless communications; and
a processor configured to:
    receive a secure package via a wireless communication from a device when the glucose monitor is uninitialized,
    extract contents of the secure package, including an initialization code and a key,
    validate the key as valid or not,
    where the key is valid,
        permitting the device to conduct wireless communications with the glucose monitor,
        validate the initialization code as valid or not,
        where the initialization code is valid, initialize the glucose monitor,
        where the initialization code is not valid, not initialize the glucose monitor, and
        where the key is not valid, not permitting the device to conduct wireless communications with the glucose monitor.

2. The glucose monitor of claim 1, wherein the extracting the contents of the secure package comprises at least one of decrypting the secure package, applying an inverse hash function to the secure package, or reversing an obfuscation of the secure package.

3. The glucose monitor of claim 1, wherein the extracting of the contents of the secure package comprises extracting a timestamp from the secure package.

4. The glucose monitor of claim 3, wherein the validating of the key comprises using the timestamp to determine if the key has expired.

5. The glucose monitor of claim 1, wherein the extracting of the contents of the secure package comprises extracting information regarding rights to be granted to the device as to wireless communications.

6. The glucose monitor of claim 1, where in the glucose monitor is a continuous glucose monitor.

7. A wearable device, comprising:
a wireless transceiver for transmitting and receiving wireless communications; and a processor configured to:
    compose a secure package that includes a key and an initialization code,
    transmit the secure package to a glucose monitor that is uninitialized to initialize the glucose monitor,
    where the key is valid and the initialization code is valid, receiving an indication from the glucose monitor that the key is valid and the initialization code is valid, and
    otherwise receiving an indication that attempt to wirelessly communicate with the glucose monitor and initialize the glucose monitor has failed.

8. The wearable device of claim 7, wherein the wearable device is one of a smartwatch, a smart bracelet, or a smart ring.

9. The wearable device of claim 7, wherein the wireless transceiver is an near field communication (NFC) transceiver.

10. The wearable device of claim 7, wherein the secure package is encrypted, hashed, and/or obfuscated.

11. The wearable device of claim 7, wherein the secure package includes a timestamp.

12. The wearable device of claim 7, wherein the secure package includes an indication of rights to be granted to the wearable device as to wireless communications with the glucose monitor.

13. The wearable device of claim 12, wherein the rights to be granted are viewing only rights.

14. The wearable device of claim 7, wherein the glucose monitor is a continuous glucose monitor (CGM).

15. A medicament delivery device, comprising:
a wireless transceiver for transmitting and receiving wireless communications; and
a processor configured to:
    receive a secure package from a requesting device,
    extract contents of the secure package, including a key and an indication of rights of the requesting device,
    validate the key as valid or not,
    where the key is valid, in view of contents of the secure package, grant only viewing rights to the requesting device so that the requesting device can read information from the medicament delivery device but is prohibited from changing values stored at the medicament delivery device and from issuing commands to the medicament delivery device; and
    where the key is not valid, not permit wireless communications between the medicament delivery device and the requesting device.

16. The medicament delivery device of claim 15, wherein the extracting the contents of the secure package comprises at least one of decrypting the secure package, applying an inverse hash function to the secure package or reversing an obfuscation of the secure package.

17. The medicament delivery device of claim 15, wherein the extracting the contents of the secure package comprises at least one of extracting a timestamp.

18. The medicament delivery device of claim 17, wherein the validating the key comprises using the timestamp to determine whether the key has expired.

19. The medicament delivery device of claim 15, wherein the requesting device is a wearable device.

20. The medicament delivery device of claim 19, wherein the requesting device is a smartwatch.

* * * * *